United States Patent [19]

Schmitz et al.

[11] 4,456,765

[45] Jun. 26, 1984

[54] TRICHOTHEC-9-ENE-3,4,15-TRIOL,12,13-EPOXY-3-CHLOROACETATE USEFUL AS AN ANTI-TUMOR AGENT

[75] Inventors: Henry Schmitz, Syracuse; Takushi Kaneko, Fayetteville; John M. Essery, Pleasantville; Terrence W. Doyle, Fayetteville, all of N.Y.

[73] Assignee: Bristol-Myers Company, New York, N.Y.

[21] Appl. No.: 506,133

[22] Filed: Jun. 20, 1983

Related U.S. Application Data

[62] Division of Ser. No. 339,581, Jan. 15, 1982, Pat. No. 4,413,134, which is a division of Ser. No. 240,340, Mar. 4, 1981, Pat. No. 4,332,732, which is a division of Ser. No. 137,336, Apr. 4, 1980, Pat. No. 4,284,568.

[51] Int. Cl.[3] .......... C07D 311/78

[52] U.S. Cl. .......... 549/332

[58] Field of Search .......... 549/332

[56] References Cited

U.S. PATENT DOCUMENTS

| | | | |
|---|---|---|---|
| 3,428,652 | 2/1969 | Sigg et al. | 549/332 |
| 4,129,577 | 12/1978 | Ellison et al. | 549/332 |
| 4,244,874 | 1/1981 | Kaneko | 549/332 |
| 4,267,113 | 5/1981 | Kaneko et al. | 549/332 |

FOREIGN PATENT DOCUMENTS

| | | | |
|---|---|---|---|
| 1063255 | 3/1967 | United Kingdom | 549/332 |

OTHER PUBLICATIONS

Wei et al., Biochem. & Biophys. Res. Comm., 57, 838, (1974).

Grove, J. Chem. Soc. (C), 375, (1970).

Pathre et al., J. Agric, Food Chem., 24, 97, (1976).

Derwent 249B2W/15 of Japanese Patent 49/134,891.

Derwent 249B3W/15 of Japanese Patent 49/134,892.

Tatsuno et al., j. Pure & Appl. Chem., 35, 309, (1973).

Grove et al., Biochem. Pharm., 24, 959, (1972).

Sigg et al., Helv. Chim. Acta, 48, 962, (1965).

Murphy et al., Proc. Amer. Assoc. Cancer Res., 17, 90, (1976).

Haas et al., ibid, 18, 296, (1977).

*Primary Examiner*—Nicky Chan
*Attorney, Agent, or Firm*—David M. Morse

[57] ABSTRACT

Novel mono-, di- and triacylated derivatives of scirpentriol are provided for use as antitumor agents. Also provided are methods for the production of such derivatives.

1 Claim, No Drawings

TRICHOTHEC-9-ENE-3,4,15-TRIOL,12,13-EPOXY-3-CHLOROACETATE USEFUL AS AN ANTI-TUMOR AGENT

This application is a division of our co-pending application Ser. No. 339,581 filed Jan. 15, 1982, now U.S. Pat. No. 4,413,134, which is a division of application Ser. No. 240,340 filed Mar. 4, 1981 now U.S. Pat. No. 4,332,732 which is a division of application Ser. No. 137,336 filed Apr. 4, 1980 now U.S. Pat. No. 4,284,568.

BACKGROUND OF THE INVENTION

1. Field of the Invention

The present invention relates to novel trichothecene derivatives, to processes for their production and to their use as antitumor agents for the inhibition of malignant tumors in mammals.

2. Description of the Prior Art

The trichothecene derivatives of the present invention in general contain a 9,10 double bond and a 12,13-epoxy function. The basic skeleton and numbering system for this class of trichothecenes is shown below.

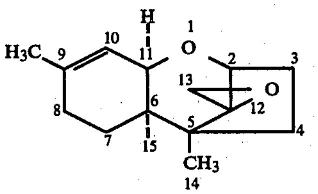

Various examples of both naturally occurring and semi-synthetic compounds of this class have been described in the literature. Illustrative of the more relevant publications are the following:

1. The compound anguidine (also called diacetoxyscirpenol) having the formula

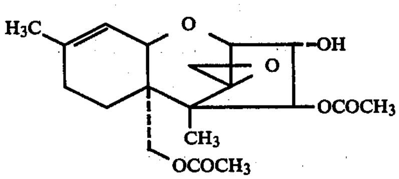

is disclosed as an antitumor agent in U.K. Pat. No. 1,063,255. Phase I clinical trials of anguidine in the United States have been reported in *Proc. Amer. Assoc. Cancer Res.* 17:90 (1976) and *Proc. Amer. Assoc. Cancer Res.* 18:296 (1977). Also disclosed (at least generically) are various derivatives of anguidine such as anguidol (also called scirpentriol or 3α,4β,15-trihydroxy-12,13-epoxytrichothec-9-ene), monodesacetylanguidine (presumably 15-acetoxy-3α,4β-dihydroxy-12,13-epoxytrichothec-9-ene or monoacetoxyscirpendiol) and esters of anguidine, anguidol and monodesacetylanguidine.

Monoacetoxyscirpenol and certain esters of scirpentriol (not including any of the presently claimed compounds) are also disclosed in *J. Agric. Food Chem.* 24(1): 97-103 (1976) as mycotoxins.

2. Japanese Published Applications No. J4 9,134,891 and No. J4 9,134,892 disclose T2 and HT2 toxins of the formula

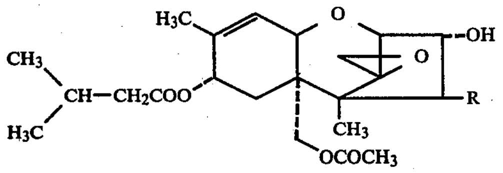

wherein R is —OH or

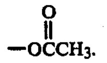

The compounds are said to be useful as antiviral agents.

3. U.S. Pat. No. 4,129,577 discloses anguidine derivatives of the formula

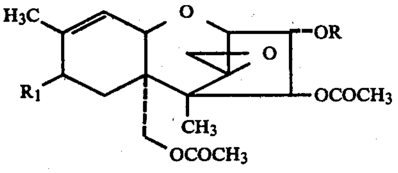

wherein $R_1$ is H or

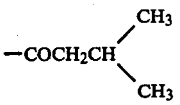

and R is an alkyl or aromatic group or is an acyl group

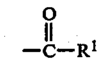

in which $R^1$ is an aliphatic, cycloaliphatic or aromatic group or a carbamate group —CONH—$R^1$. The compounds are useful as cytotoxic agents.

4. U.S. Pat. No. 3,428,652 discloses anguidine derivatives of the formula

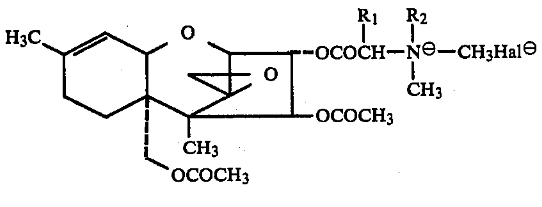

wherein $R_1$ is H and $R_2$ is methyl or, $R_1$ and $R_2$ together represent propylene, and Hal is Cl, Br or I. The compounds are reported to have antitumor activity.

5. The 12,13-epoxytrichothecenes of the general formula

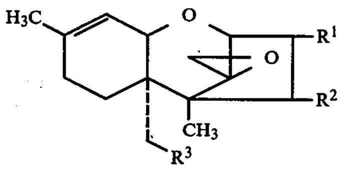

wherein $R^1$ and $R^3$ are H, OH or esterified OH and $R^2$ is OH, =O or esterified OH are described in *Biochemical and Biophysical Research Communications* 57(3):838-844 (1974) as inhibitors of protein synthesis. None of the ester derivatives of the present invention are disclosed in this publication.

SUMMARY OF THE INVENTION

The present invention provides novel mono-, di- and triacylated derivatives of scirpentriol which may be represented by the general formula

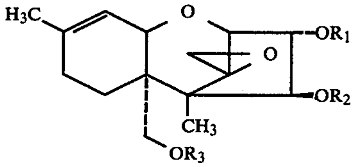

I in which $R_1$, $R_2$ and $R_3$ are hydrogen or the residue of certain ester groups and at least one of $R_1$, $R_2$ or $R_3$ is other than hydrogen.

More specifically, the present invention provides (1) monoacylated ester derivatives of the formula

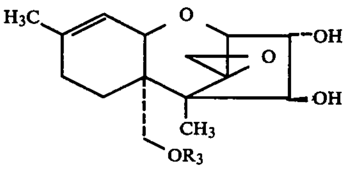

IIA in which $R_3$ is $-COCH_2Cl$, $-COCH{=}CHCH_3$, $-COCCH_3{=}CH_2$, $-COC_6H_5$ or $-COCHClCH_3$;

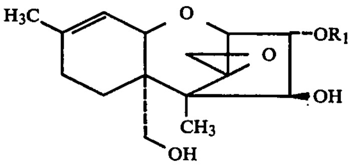

IIB in which $R_1$ is $-COCH_2Cl$; and

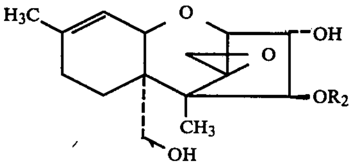

IIC in which $R_2$ is $-COCH_2Cl$; (2) diacylated ester derivatives of the formulae

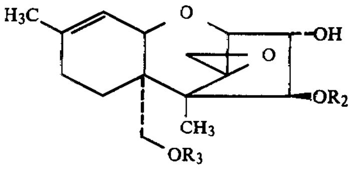

IIIA in which $R_2$ and $R_3$ are each $-COCH_2Cl$; $R_2$ and $R_3$ are each $-COCH{=}CHCH_3$; $R_2$ is $-COCH_2Cl$ and $R_3$ is $-COCH_3$; or $R_2$ is $-COCH_2Cl$ and $R_3$ is $-COCCH_3{=}CH_2$; and

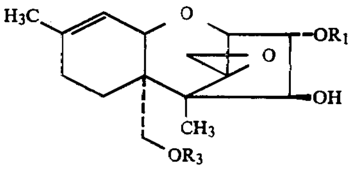

IIIB in which $R_1$ and $R_3$ are each $-COCH_2Cl$; (3) the triacylated ester derivative of the formula

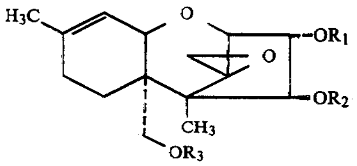

IV in which $R_1$, $R_2$ and $R_3$ are each $-COCH_2Cl$; and (4) the monoacylated ester epoxy derivative of the formula

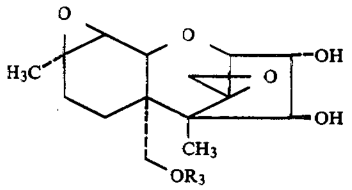

V in which $R_3$ is $-COCH{=}CHCH_3$.

The ester derivatives of formula II-V are antitumor agents for treatment of malignant tumors in mammals.

As denoted by the structural formulae above, the compounds of formulae II-V all have the α-configuration at the 3-substituent and the β-configuration at the 4-substituent.

DETAILED DESCRIPTION

The ester derivatives of the present invention may be prepared by methods known in the art. Illustrative of such methods are the reaction schemes shown below.

Scheme 1

Preparation of Starting Materials

-continued
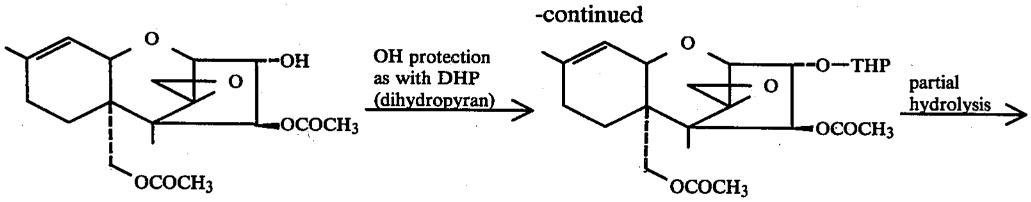
anguidine
1
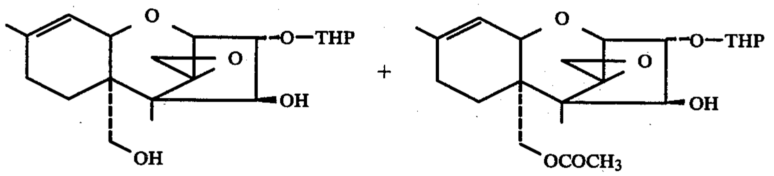
2
3
Scheme 2
Esterification of Scirpentriol
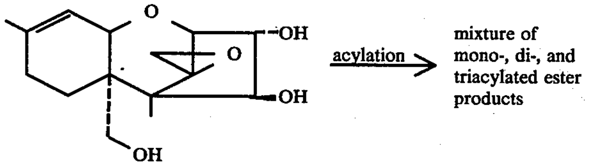
Scheme 3
Esterification of 3α-hydroxy-protected diol 2 to produce diacylated esters
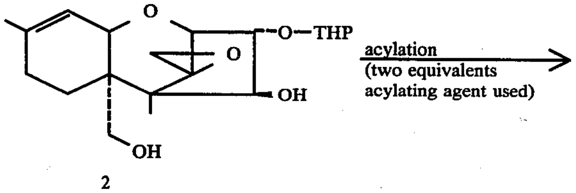
2
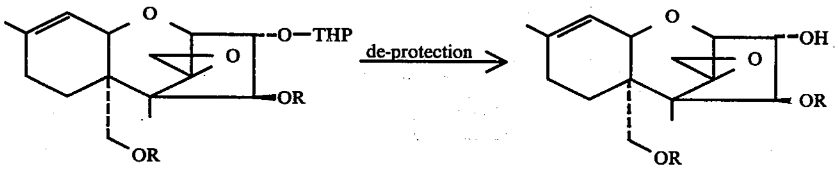
Scheme 4
Esterification of starting material 5 to produce diacylated esters where $R_3$ in formula IIIA is $-COCH_3$
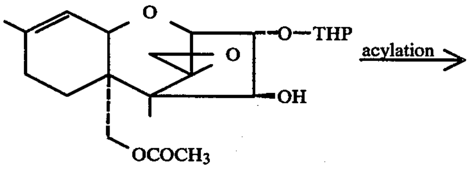
5
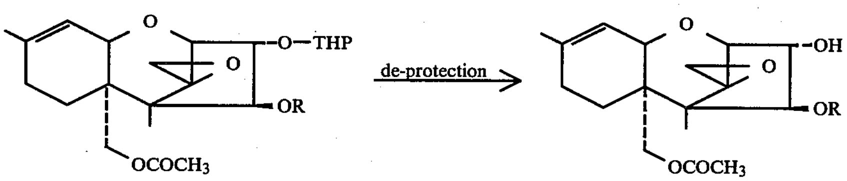
Scheme 5
Esterification of 3α-hydroxy-protected diol 2 to produce monoacylated esters -continued
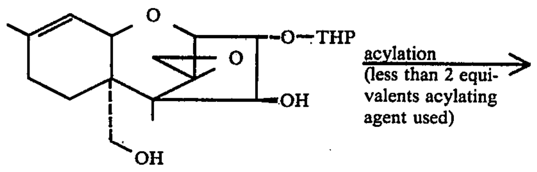
2
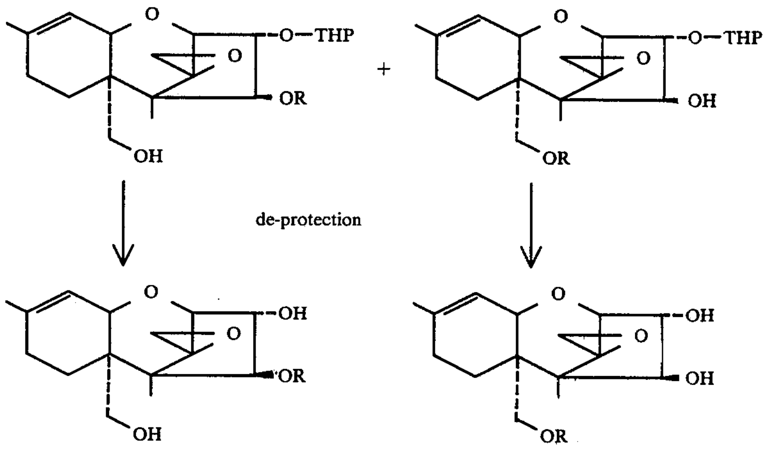
Scheme 6
Preparation of 4,15-dicacylated esters of formula IIIA where $R_2 \neq R_3$
(A)
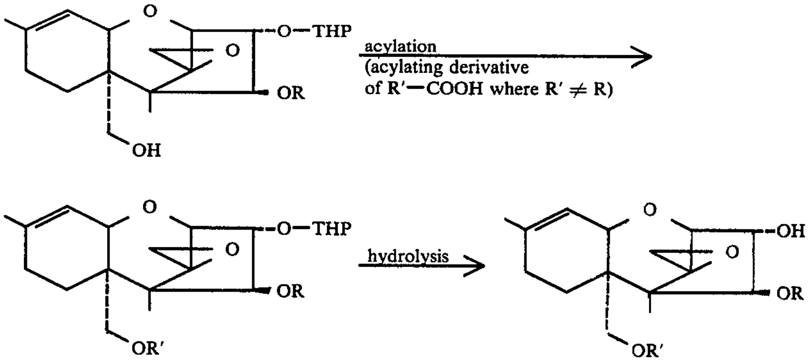
(B)
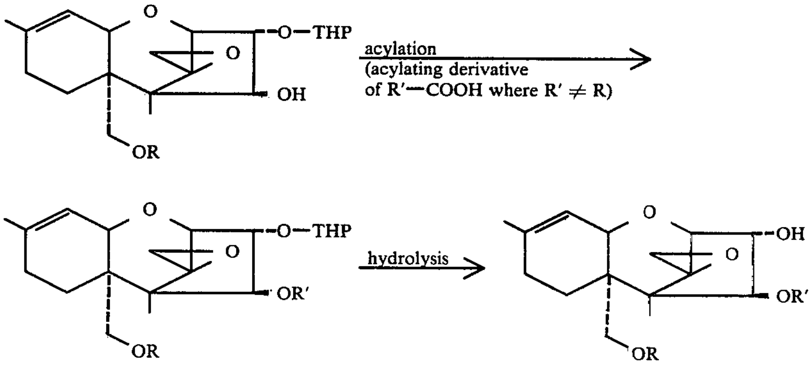
Scheme 7
Epoxidation to produce 9,10-epoxide -continued

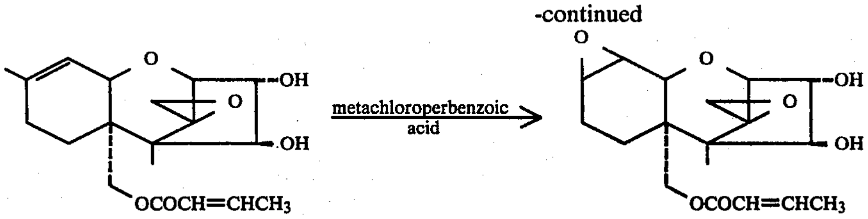

EXPLANATION OF SCHEMES 1-7

In general, the esters of the present invention may be prepared by acylation of scirpentriol or the 3-tetrahydropyran-protected derivatives 2 and 3. To prepare 3-tetrahydropyran (THP)-protected derivatives 2 and 3, the 3α-OH group of anguidine is protected as by conversion to a tetrahydropyranyl ether 1 and this 3α-OTHP derivative is then subjected to partial basic hydrolysis to give a mixture of the 4β-OH (3) and 4β,15-OH (2) derivatives.

In Scheme 2, scirpentriol may be acylated in accordance with conventional methods with a suitable acylating derivative of a carboxylic acid R—COOH to produce a mixture of the various mono-, di- and triacylated derivatives. The desired product is then separated from the product mixture as by silica gel column chromatography. The acylation is typically carried out with an acid halide or acid anhydride, preferably in the presence of an organic base such as pyridine or lutidine. An inert organic solvent such as methylene chloride may be employed or the organic base may also serve as a reaction solvent.

Scheme 3 shows the acylation of diol intermediate 2 with two or more equivalents of acylating agent followed by hydrolysis of the 3α-OTHP group to give 4,15-diacylated esters of formula IIIA having $R_2=R_3$. The acylation procedure is carried out by conventional procedures such as described for Scheme 2.

Scheme 4 illustrates a procedure for preparing a 4,15-diacylated ester of formula IIIA where $R_3$ is $—COCH_3$. In this procedure starting material 5 is acylated as described above to give a 3α-THP derivative which is hydrolyzed to produce the desired product.

If diol intermediate 2 is acylated with less than two equivalents of acylating agent as in Scheme 5, there may be produced after the usual de-blocking step a mixture of 4- and 15-monoacylated products. These products can then be separated as by chromatography.

Scheme 6 shows that the monoacylated 3α-THP intermediate as produced in Scheme 5 can be treated with a second acylating agent to give after the de-protection step a diacylated ester of formula IIIA where $R_2 \neq R_3$.

Finally, Scheme 7 illustrates epoxidation of a 15-monoacylated ester with metachloroperbenzoic acid to give the corresponding 9,10-epoxide.

Biological Activity

Representative compounds of the present invention were tested for antitumor activity against the transplantable mouse tumors P-388 leukemia, L-1210 leukemia and Lewis lung carcinoma and the results of these tests are shown below in Tables I-XVIII. The methodology used generally followed the protocols of the National Cancer Institute (see, for example, *Cancer Chemotherapy Rep.* Part 3, 3:1-103 (1972)). The essential experimental details are given at the bottom of the tables.

TABLE 1

Effect of Compound of Example 1E on P-388 Leukemia

| Compound | Dose mg/kg/day | MST Days | Effect MST % T/C | Average Weight Change, g | Survivors Day 5 |
|---|---|---|---|---|---|
| NSC-38270* | 0.4 | 15.5 | 172 | +0.5 | 6/6 |
| | 0.2 | 12.5 | 139 | +0.8 | 6/6 |
| NSC-141537 | 0.8 | 12.5 | 139 | +0.3 | 6/6 |
| (Anguidine) | 0.4 | 11.0 | 122 | −0.3 | 6/6 |
| | 0.2 | 9.5 | 100 | −0.3 | 6/6 |
| | 0.1 | 9.0 | 100 | −0.3 | 6/6 |
| Compound of | 6.4 | 18.5 | 206 | −0.3 | 6/6 |
| Example 1E | 3.2 | 16.0 | 178 | −0.3 | 6/6 |
| | 1.6 | 14.0 | 156 | −3.1 | 6/6 |
| | 0.8 | 12.5 | 139 | +1.5 | 6/6 |
| | 0.4 | 12.5 | 139 | +0.4 | 6/6 |
| | 0.2 | 10.5 | 117 | 0.4 | 6/6 |
| Control | Saline | 9.0 | — | +0.7 | 10/10 |

Tumor inoculum $10^6$ ascites cells implanted i.p.
Host $CDF_1$ ♂ mice.
Treatment QD 1→9.
Evaluation MST = median survival time.
Effect % T/C = MST treated/MST control × 100.
Criteria T/C≧125 considered significant antitumor effect.
*NSC-38270 used in this and the following tables is a crude (~40%) preparation of olivomycin A which is used as a reference in screening of anguidine derivatives.

TABLE II

Effect of Compound of Example 1C on P-388 Leukemia

| Material | Dose mg/kg/day | MST Days | Effect MST % T/C | Average Weight Change, g | Survivors Day 5 |
|---|---|---|---|---|---|
| NSC-38270 | 0.4 | 14.0 | 156 | +0.6 | 6/6 |
| | 0.2 | 12.5 | 139 | +0.8 | 6/6 |
| NSC-141537 | 1.6 | 16.5 | 183 | −0.1 | 6/6 |
| (Anguidine) | 0.8 | 15.0 | 167 | +0.4 | 6/6 |
| | 0.4 | 13.0 | 144 | +1.3 | 6/6 |
| | 0.2 | 11.5 | 128 | +0.5 | 6/6 |
| | 0.1 | 11.0 | 122 | +1.0 | 6/6 |
| | 0.05 | 9.5 | 106 | +0.8 | 6/6 |
| Compound of | 6.4 | 14.5 | 161 | −0.5 | 6/6 |
| Example 1C | 3.2 | 14.5 | 161 | +0.3 | 6/6 |
| | 1.6 | 12.5 | 139 | +0.4 | 6/6 |
| | 0.8 | 12.0 | 133 | +0.6 | 6/6 |
| | 0.4 | 11.0 | 122 | +0.3 | 6/6 |
| | 0.2 | 10.5 | 117 | +0.3 | 6/6 |
| | 0.1 | 10.0 | 111 | +0.6 | 6/6 |
| | 0.05 | 10.0 | 111 | +0.8 | 6/6 |
| | 0.025 | 9.0 | 100 | +1.0 | 6/6 |
| | 0.0125 | 9.0 | 100 | +0.8 | 6/6 |
| Control | 0.5 | 9.0 | — | +0.5 | 10/10 |

Tumor inoculum $10^6$ ascites cells implanted i.p.
Host $CDF_1$ ♀ mice.
Treatment QD 1→9.
Evaluation MST = median survival time.
Effect % T/C = MST treated/MST control × 100.
Criteria T/C≧125 considered significant antitumor effect.

TABLE III

Effect of Compound of Example 9 on P-388 Leukemia

| Compound | Dose mg/kg/day | MST Days | Effect MST % T/C | Average Weight Change, g | Survivors Day 5 |
|---|---|---|---|---|---|
| NSC-38270 | 0.4 | 13.0 | 144 | −0.7 | 6/6 |

TABLE III-continued

Effect of Compound of Example 9 on P-388 Leukemia

| Compound | Dose mg/kg/day | MST Days | Effect MST % T/C | Average Weight Change, g | Survivors Day 5 |
|---|---|---|---|---|---|
| | 0.2 | 11.0 | 122 | −0.5 | 6/6 |
| NSC-141537 | 3.2 | 17.5 | 194 | +0.6 | 6/6 |
| (Anguidine) | 1.6 | 17.5 | 194 | +0.2 | 6/6 |
| | 0.8 | 15.0 | 167 | +0.4 | 6/6 |
| | 0.4 | 14.5 | 161 | +0.5 | 6/6 |
| | 0.2 | 13.5 | 150 | +1.0 | 6/6 |
| | 0.1 | 11.0 | 122 | +0.1 | 6/6 |
| | 0.05 | 11.0 | 122 | +0.2 | 5/5 |
| | 0.025 | 9.5 | 106 | +0.5 | 6/6 |
| Compound of | 3.2 | 16.5 | 183 | +0.8 | 6/6 |
| Example 9 | 1.6 | 16.0 | 178 | +1.0 | 6/6 |
| | 0.8 | 16.0 | 178 | +1.3 | 6/6 |
| | 0.4 | 14.5 | 161 | +0.4 | 6/6 |
| | 0.2 | 12.0 | 133 | +0.7 | 6/6 |
| | 0.1 | 12.0 | 133 | +0.8 | 6/6 |
| | 0.05 | 10.5 | 117 | +0.3 | 6/6 |
| | 0.025 | 10.5 | 117 | +0.3 | 6/6 |
| | 0.0125 | 10.0 | 111 | +0.3 | 6/6 |
| | 0.00625 | 10.0 | 111 | +0.8 | 6/6 |
| Control | DMSO-HPC | 9.0 | — | +0.4 | 10/10 |

Tumor inoculum $10^6$ ascites cells implanted i.p.
Host $CDF_1$ ♀ mice.
Treatment QD 1→9.
Evaluation MST = median survival time.
Effect % T/C = MST treated/MST control = 100.
Criteria T/C ≧125 considered significant antitumor effect.

TABLE IV

Effect of Derivatives on P-388 Leukemia

| Compound | Dose mg/kg/day | MST Days | Effect MST % T/C | Average Weight Change, g | Survivors Day 5 |
|---|---|---|---|---|---|
| NSC-38270 | 0.4 | 12.5 | 139 | +0.3 | 6/6 |
| | 0.2 | 11.0 | 122 | +1.3 | 6/6 |
| NSC-141537 | 1.6 | 17.0 | 189 | +0.8 | 6/6 |
| (anguidine) | 0.8 | 15.0 | 167 | +1.0 | 6/6 |
| | 0.4 | 13.5 | 150 | +1.6 | 6/6 |
| | 0.2 | 13.0 | 144 | +1.5 | 6/6 |
| | 0.1 | 11.0 | 122 | +1.4 | 6/6 |
| | 0.05 | 11.0 | 122 | +1.8 | 6/6 |
| Compound of | 6.4 | 14.0 | 156 | +0.9 | 6/6 |
| Example 1D | 3.2 | 13.0 | 144 | +1.3 | 6/6 |
| | 1.6 | 12.5 | 139 | +2.8 | 6/6 |
| | 0.8 | 12.5 | 139 | +2.3 | 6/6 |
| | 0.4 | 11.5 | 128 | +1.6 | 6/6 |
| | 0.2 | 10.5 | 117 | +1.2 | 6/6 |
| Compound of | 6.4 | 17.5 | 194 | +1.2 | 6/6 |
| Example 1B | 3.2 | 14.0 | 156 | +3.0 | 5/5 |
| | 1.6 | 13.0 | 144 | +1.5 | 6/6 |
| | 0.8 | 12.0 | 133 | +1.7 | 6/6 |
| | 0.4 | 12.0 | 133 | +1.7 | 6/6 |
| | 0.2 | 10.0 | 111 | +1.4 | 6/6 |
| Compound of | 6.4 | 16.0 | 178 | −0.9 | 6/6 |
| Example 8 | 3.2 | 14.0 | 156 | −0.6 | 6/6 |
| | 1.6 | 13.0 | 144 | −0.1 | 6/6 |
| | 0.8 | 12.0 | 133 | −0.3 | 6/6 |
| | 0.4 | 12.5 | 139 | −0.7 | 6/6 |
| | 0.2 | 11.5 | 128 | −0.3 | 6/6 |
| | 0.1 | 13.0 | 144 | −0.6 | 6/6 |
| | 0.5 | 11.0 | 122 | −0.5 | 6/6 |
| | 0.025 | 10.0 | 111 | −0.1 | 6/6 |
| | 0.0125 | 10.0 | 111 | −0.4 | 6/6 |
| Control | Saline | | — | +0.5 | 10/10 |

Tumor inoculum $10^6$ ascites cells implanted i.p.
Host $CDF_1$ ♂ mice.
Treatment QD 1→9.
Evaluation MST = median survival time.
Effect % T/C = MST Treated/MST control × 100.
Criteria T/C≧125 considered significant antitumor effect.

TABLE V

Effect of Compound of Example 1A on P-388 Leukemia

| Compound | Dose mg/kg/day | MST Days | Effect MST % T/C | Average Weight Change, g | Survivors Day 5 |
|---|---|---|---|---|---|
| NSC-38270 | 0.4 | 13.0 | 144 | +0.1 | 5/5 |
| | 0.2 | 11.0 | 122 | +0.3 | 6/6 |
| NSC-141537 | 3.2 | 17.5 | 194 | +0.7 | 6/6 |
| (anguidine) | 1.6 | 17.0 | 189 | +0.7 | 6/6 |
| | 0.8 | 14.0 | 156 | +1.8 | 6/6 |
| | 0.4 | 13.5 | 150 | +1.9 | 6/6 |
| | 0.2 | 12.0 | 133 | +0.8 | 6/6 |
| | 0.1 | 11.0 | 122 | +1.0 | 6/6 |
| | 0.05 | 11.5 | 128 | +1.2 | 6/6 |
| | 0.025 | 10.0 | 111 | +1.3 | 6/6 |
| Compound of | 12.8 | Tox | Tox | Tox | 2/6 |
| Example 1A | 6.4 | Tox | Tox | Tox | 2/6 |
| | 3.2 | 17.5 | 194 | +0.5 | 6/6 |
| | 1.6 | 17.0 | 189 | +1.3 | 6/6 |
| | 0.8 | 14.5 | 161 | +1.8 | 6/6 |
| | 0.4 | 16.0 | 178 | +1.4 | 6/6 |
| | 0.2 | 14.0 | 156 | +0.8 | 6/6 |
| | 0.1 | 13.0 | 144 | +1.3 | 6/6 |
| | 0.05 | 13.5 | 150 | +1.3 | 6/6 |
| | 0.025 | 12.5 | 139 | +1.4 | 6/6 |
| | 0.0125 | 10.5 | 117 | +1.3 | 6/6 |
| | 0.00625 | 10.5 | 117 | +1.7 | 6/6 |
| Control | Saline | 9.0 | — | +0.6 | 10/10 |

Tumor inoculum $10^6$ ascites cells implanted i.p.
Host $CDF_1$ mice.
Treatment Daily, QD 1→9.
Tox Toxicity <4/6 survivors, Day 5.
Evaluation MST = median survival time.
Effect % T/C = MST treated/MST control × 100.
Criteria T/C ≧125 considered significant antitumor effect.

TABLE VI

Effect of Compound of Example 2 on P-388 Leukemia

| Material | Dose mg/kg/day | MST Days | Effect MST % T/C | Average Weight Change, g | Survivors Day 5 |
|---|---|---|---|---|---|
| NSC-38270 | 0.4 | 13.0 | 153 | +0.4 | 6/6 |
| A649 | 0.2 | 10.0 | 118 | +1.2 | 6/6 |
| NSC-141537 | 1.6 | 16.0 | 188 | +1.0 | 6/6 |
| Anguidine | 0.8 | 14.0 | 165 | +0.9 | 6/6 |
| | 0.4 | 13.0 | 153 | +1.3 | 6/6 |
| | 0.2 | 12.0 | 141 | +1.0 | 6/6 |
| | 0.1 | 11.0 | 129 | +0.4 | 6/6 |
| | 0.05 | 10.0 | 118 | +1.1 | 6/6 |
| Compound | 6.4 | 18.0 | 212 | −0.3 | 5/6 |
| of Exam- | 3.2 | 16.5 | 194 | +1.0 | 6/6 |
| ple 2 | 1.6 | 15.5 | 182 | +1.1 | 6/6 |
| | 0.8 | 14.0 | 165 | +1.3 | 6/6 |
| | 0.4 | 13.0 | 153 | +0.8 | 6/6 |
| | 0.2 | 13.0 | 153 | +0.2 | 6/6 |
| | 0.1 | 11.5 | 135 | +0.8 | 6/6 |
| | 0.05 | 12.5 | 147 | +0.9 | 6/6 |
| | 0.025 | 10.0 | 118 | +1.1 | 6/6 |
| | 0.0125 | 9.0 | 106 | +2.4 | 6/6 |
| | 0.00625 | 9.0 | 106 | +2.3 | 6/6 |
| | 0.003125 | 9.0 | 106 | +3.1 | 6/6 |
| Control | Saline | 8.5 | — | +3.1 | 10/10 |

Tumor inoculum $10^6$ ascites cells implanted i. p.
Host $CDF_1$ ♂ mice.
Treatment QD 1→9.
Evaluation MST = median survival time.
Effect % T/C = MST treated/MST control × 100.
Criteria T/C≧125 considered significant antitumor effect.

TABLE VII

Effect of Compound of Example 2 on P-388 Leukemia

| Material | Treatment | Dose, IP mg/kg/day | MST Days | Effect MST % T/C | Average Weight Change, g | Survivors Day 5 (30) |
|---|---|---|---|---|---|---|
| NSC 38270 | Days 1→9 | 0.4 | 11.5 | 128 | −1.5 | 6/6 |
| | | 0.2 | 10.0 | 111 | −0.9 | 6/6 |
| Anguidine | Day 1 only | 20 | Tox | Tox | Tox | 0/6 |
| NSC 141537 | | 16 | Tox | Tox | Tox | 0/6 |
| | | 12 | Tox | Tox | Tox | 2/6 |
| | | 8 | Tox | Tox | Tox | 3/6 |
| | Days 1→5 | 5 | Tox | Tox | Tox | 3/6 |
| | | 4 | 15.0 | 167 | +0.3 | 6/6 |
| | | 3 | 14.0 | 156 | +0.3 | 6/6 |
| | | 2 | 13.0 | 144 | +0.2 | 6/6 |
| | Days 1→9 | 2.4 | 16.0 | 178 | +1.3 | 6/6 |
| | | 1.6 | 16.0 | 178 | +0.6 | 5/5 |
| Compound of | Day 1 only | 60 | Tox | Tox | Tox | 0/6 |
| Example 2 | | 45 | Tox | Tox | Tox | 0/6 |
| | | 30 | Tox | Tox | Tox | 1/6 |
| | | 20 | Tox | Tox | Tox | 0/6 |
| | Days 1→5 | 12 | Tox | Tox | Tox | 2/6 |
| | | 10 | Tox | Tox | Tox | 1/6 |
| | | 8 | 13.0 | 144 | −1.5 | 5/6 |
| | | 6.4 | 13.5 | 150 | −0.8 | 4/6 |
| | Days 1→9 | 9.0 | Tox | Tox | Tox | 3/6 |
| | | 6.4 | 12.0 | 133 | +0.3 | 6/6 |
| Control | | Saline | 9.0 | — | +2.2 | 10/10 |

Tumor inoculum $10^6$ ascites cells implanted i.p.
Host $CDF_1$ ♂ mice.
Tox <4/6 survivors Day 5.
Evaluation MST = median survival time.
Effect % T/C = (MST treated/MST control) × 100.
Criteria % T/C≧125 considered significant antitumor activity.

TABLE VIII

Effect of Compound of Example 2 on P-388 Leukemia

| Material | Dose mg/kg/inj | MST Days | Effect MST % T/C | Average Weight Change, g | Survivors Day 5 |
|---|---|---|---|---|---|
| NSC-141537 | 1.6 | 11.0 | 183 | +0.5 | 6/6 |
| (Anguidine) | 0.8 | 8.5 | 142 | +1.2 | 6/6 |
| | 0.4 | 8.5 | 142 | +1.2 | 6/6 |
| | 0.2 | 8.0 | 133 | +1.5 | 6/6 |
| | 0.1 | 7.0 | 117 | +1.9 | 6/6 |
| | 0.05 | 7.0 | 117 | +2.6 | 6/6 |
| Compound of | 12.8 | 8.5 | 142 | −0.9 | 4/6 |
| Example 2 | 6.4 | 10.5 | 175 | −0.2 | 6/6 |
| | 3.2 | 9.5 | 158 | +1.0 | 6/6 |
| | 1.6 | 9.5 | 158 | +1.8 | 6/6 |
| | 0.8 | 8.5 | 142 | −1.3 | 6/6 |
| | 0.4 | 8.5 | 142 | −0.7 | 6/6 |
| | 0.2 | 7.0 | 117 | +0.3 | 6/6 |
| | 0.1 | 7.0 | 117 | +0.3 | 6/6 |
| Control | Saline | 6.0 | — | +2.5 | 10/10 |

Tumor inoculum $10^6$ ascites cells implanted i.p.
Host $BDF_1$ ♂ mice.
Treatment Daily, QD 1→9.
Evaluation MST = median survival time.
Effect % T/C = MST treated/MST control × 100.
Criteria T/C≧125 considered significant antitumor effect.

TABLE IX

Effect of Compound of Example 4 on P-388 Leukemia

| Material | Dose mg/kg/day | MST Days | Effect MST % T/C | Average Weight Change, g | Survivors Day 5 |
|---|---|---|---|---|---|
| NSC-38270 | 0.4 | 12.0 | 133 | +0.7 | 6/6 |
| (A-649) | 0.2 | 11.0 | 122 | −0.4 | 6/6 |
| NSC-141537 | 1.6 | 17.0 | 189 | +1.3 | 5/5 |
| (anguidine) | 0.8 | 14.0 | 156 | +1.7 | 5/6 |
| | 0.4 | 14.0 | 156 | +1.9 | 6/6 |
| | 0.2 | 12.0 | 133 | +1.5 | 6/6 |
| | 0.1 | 11.5 | 128 | +0.8 | 6/6 |
| | 0.05 | 10.0 | 111 | +0.3 | 6/6 |
| Compound of | 6.4 | Tox | Tox | Tox | 1/6 |
| Example 4 | 3.2 | 20.0 | 222 | −1.9 | 5/6 |
| | 1.6 | 17.0 | 189 | −0.9 | 6/6 |

TABLE IX-continued

Effect of Compound of Example 4 on P-388 Leukemia

| Material | Dose mg/kg/day | MST Days | Effect MST % T/C | Average Weight Change, g | Survivors Day 5 |
|---|---|---|---|---|---|
| | 0.8 | 14.5 | 161 | +0.9 | 6/6 |
| | 0.4 | 13.0 | 144 | +0.2 | 5/6 |
| | 0.2 | 12.5 | 139 | 0 | 6/6 |
| | 0.1 | 13.0 | 144 | 0 | 6/6 |
| | 0.05 | 11.0 | 122 | −0.8 | 6/6 |
| | 0.025 | 11.0 | 122 | −0.3 | 6/6 |
| | 0.0125 | 11.0 | 122 | −0.4 | 6/6 |
| Control | Saline | 9.0 | — | +0.3 | 10/10 |

Tumor inoculum $10^6$ ascites cells implanted i.p.
Host $CDF_1$ ♂ mice.
Treatment Daily, QD 1→9.
Tox Toxicity, 4/6 survivors Day 5.
Evaluation MST = median survival time.
Effect % T/C = MST treated/MST control × 100.
Criteria T/C ≧125 considered significant antitumor effect.

TABLE X

Effect of Compound of Example 4 on L-1210 Leukemia

| Material | Dose, IP mg/kg/day | MST Days | Effect MST % T/C | Average Weight Change, g | Survivors Day 5 (30) |
|---|---|---|---|---|---|
| Anguidine | 2.0 | 11.0 | 157 | −0.8 | 6/6 |
| NSC | 1.6 | 11.0 | 157 | −0.3 | 6/6 (1/6) |
| 141537 | 1.2 | 11.0 | 157 | −0.3 | 6/6 |
| | 0.8 | 11.0 | 157 | −0.3 | 6/6 |
| | 0.4 | 10.0 | 143 | −0.1 | 6/6 |
| | 0.2 | 9.0 | 129 | +0.5 | 6/6 (1/6) |
| Compound | 1.6 | 12.0 | 171 | −0.8 | 4/6 (2/6) |
| pf Exam- | 0.8 | 10.0 | 143 | −0.3 | 6/6 |
| ple 4 | 0.4 | 9.5 | 136 | −0.8 | 6/6 |
| | 0.2 | 9.0 | 129 | −0.3 | 6/6 |

TABLE X-continued

Effect of Compound of Example 4 on L-1210 Leukemia

| Material | Dose, IP mg/kg/day | MST Days | Effect MST % T/C | Average Weight Change, g | Survivors Day 5 (30) |
|---|---|---|---|---|---|
| Control | Saline | 7.0 | — | +0.9 | 10/10 |

Tumor inoculum $10^6$ ascites cells implanted i.p.
Host $BDF_1$ ♂ mice.
Treatment QD 1→9.
Tox <4/6 mice alive on Day 5.
Evaluation MST = median survival time.
Effect % T/C = (MST treated/MST control) × 100.
Criteria % T/C≧125 considered significant antitumor activity.

TABLE XI

Effect of Derivatives on L-1210 Leukemia

| Material | Dose mg/kg/day | MST Days | Effect MST % T/C | Average Weight Change, g | Survivors Day 5 |
|---|---|---|---|---|---|
| Anguidine | 2.0 | 6.0 | 86 | −0.9 | 4/6 |
| NSC 141537 | 1.6 | 6.0 | 86 | −1.3 | 6/6 |
| | 1.2 | 11.0 | 157 | −1.1 | 5/6 |
| | 0.8 | 11.0 | 157 | +1.0 | 5/6 |
| Compound of | 4.0 | Tox | Tox | Tox | 0/6 |
| Example 4 | 3.2 | Tox | Tox | Tox | 0/6 |
| | 2.4 | Tox | Tox | Tox | 2/6 |
| | 1.6 | Tox | Tox | Tox | 3/6 |
| Compound of | 2.4 | 6.0 | 86 | −1.5 | 5/6 |
| Example 3 | 1.6 | 6.0 | 86 | −1.3 | 6/6 |
| | 1.2 | 8.0 | 114 | 6/6 | |
| | | | −0.6 | | |
| | 0.8 | 12.0 | 171 | −2.6 | 6/6 |
| Compound of | 0.6 | Tox | Tox | Tox | 3/6 |
| Example 6 | 0.4 | 10.0 | 143 | −1.1 | 5/6 |
| | 0.3 | 10.5 | 150 | −1.0 | 4/6 |
| | 0.2 | 10.0 | 143 | +0.1 | 5/6 |
| Control | Saline | 7.0 | — | +2.4 | 10/10 |

Tumor inoculum: $10^6$ ascitic cells implanted ip
Host: $BDF_1$ ♀ mice.
Treatment: QD 1→9
Tox: <4/6 survivors Day 5
Evaluation: % T/C = MST treated/MST control × 100.
Criteria: % T/C ≧125 considered significant antitumor effect.

TABLE XII

Effect of Compound of Example 3 on P-388 Leukemia

| Material | Dose mg/kg/day | MST Days | Effect MST % T/C | Average Weight Change, g | Survivor Day 5 |
|---|---|---|---|---|---|
| NSC-38270 | 0.4 | 12.5 | 139 | −0.6 | 6/6 |
| | 0.2 | 11.0 | 122 | +0.3 | 6/6 |
| NSC-141537 | 1.6 | 15.0 | 167 | −0.2 | 6/6 |
| (anguidine) | 0.8 | 14.0 | 156 | +0.5 | 6/6 |
| | 0.4 | 17.0 | 189 | +0.2 | 6/6 |
| | 0.2 | 16.5 | 183 | −0.5 | 6/6 |
| | 0.1 | 11.0 | 122 | +0.7 | 6/6 |
| | 0.05 | 10.5 | 117 | +0.6 | 6/6 |
| Compound of | 6.4 | 7.0 | 78 | −2.0 | 5/6 |
| Example 3 | 3.2 | 7.5 | 83 | −1.0 | 6/6 |
| | 1.6 | 20.0 | 222 | −0.6 | 6/6 |
| | 0.8 | 19.5 | 217 | +0.1 | 6/6 |
| | 0.4 | 17.0 | 189 | +0.5 | /66 |
| | 0.2 | 15.5 | 172 | −0.1 | 6/6 |
| | 0.1 | 14.5 | 161 | +0.1 | 6/6 |
| | 0.05 | 13.0 | 144 | +0.1 | 6/6 |
| | 0.025 | 12.0 | 133 | −0.2 | 6/6 |
| | 0.0125 | 10.5 | 117 | +0.6 | 6/6 |
| Control | Saline | 9.0 | — | 0 | 10/10 |

Tumor inoculum: $10^6$ ascites cells implanted i.p.
Host: $CDF_1$ ♀ mice.
Treatment: QD 1→9.
Tox: Toxicity, <4/6 survivors, Day 5.
Evaluation: MST = median survival time.
Effect: % T/C = MST treated/MST control × 100.
Criteria: T/C ≧125 considered significant antitumor effect.

TABLE XIII

Effect of Compound of Example 5 on P-388 Leukemia

| Material | Dose mg/kg/day | MST Days | Effect MST % T/C | Average Weight Change, g | Survivors Day 5 |
|---|---|---|---|---|---|
| NSC-38270 | 0.4 | 11.0 | 122 | −0.4 | 6/6 |
| | 0.2 | 9.5 | 106 | +0.1 | 6/6 |
| Compound of | 6.4 | 15.0 | 167 | −0.4 | 5/6 |
| Example 5 | 3.2 | 14.5 | 161 | 0 | 6/6 |
| | 1.6 | 13.0 | 144 | +1.5 | 5/6 |
| | 0.8 | 10.0 | 111 | +0.8 | 6/6 |
| | 0.4 | 9.0 | 100 | +1.2 | 6/6 |
| | 0.2 | 9.5 | 106 | +2.8 | 6/6 |
| | 0.1 | 10.0 | 111 | +2.9 | 6/6 |
| | 0.05 | 9.0 | 100 | +3.1 | 6/6 |
| NSC-141537 | 1.6 | 15.0 | 167 | +1.5 | 6/6 |
| (Anguidine) | 0.8 | 15.0 | 167 | +1.6 | 6/6 |
| | 0.4 | 14.0 | 156 | +1.2 | 6/6 |
| | 0.2 | 12.0 | 133 | +0.8 | 6/6 |
| | 0.1 | 10.5 | 117 | +1.4 | 6/6 |
| | 0.05 | 10.0 | 111 | +1.5 | 6/6 |
| Control | Saline | 9.0 | — | +3.7 | 10/10 |

Tumor inoculum: $10^6$ ascites cells implanted i.p.
Host: $CDF_1$ ♀ mice.
Treatment: QD 1→9.
Evaluation: MST = median survival time.
Effect: % T/C = MST treated/MST control × 100.
Criteria: T/C ≧125 considered significant antitumor effect.

TABLE XIV

Effect of Compound of Example 6 on P-388 Leukemia

| Material | Dose mg/kg/day | MST Days | Effect MST % T/C | Average Weight Change, g | Survivors Day 5 |
|---|---|---|---|---|---|
| NSC-38270 | 0.4 | 11.0 | 138 | −1.0 | 6/6 |
| | 0.2 | 10.0 | 125 | −0.2 | 6/6 |
| Anguidine | 1.6 | 15.0 | 188 | +0.6 | 6/6 |
| NSC 141537 | 0.8 | 13.0 | 163 | +0.7 | 6/6 |
| | 0.4 | 13.0 | 163 | +0.3 | 6/6 |
| | 0.2 | 12.0 | 150 | +0.8 | 6/6 |
| | 0.1 | 10.0 | 125 | +0.1 | 6/6 |
| | 0.05 | 10.0 | 125 | +0.4 | 6/6 |
| Compound of | 12.8 | Tox | Tox | Tox | 0/6 |
| Example 6 | 6.4 | Tox | Tox | Tox | 0/6 |
| | 3.2 | Tox | Tox | Tox | 0/6 |
| | 1.6 | Tox | Tox | Tox | 0/6 |
| | 0.8 | 6.0 | 75 | −1.9 | 4/6 |
| | 0.4 | 18.0 | 225 | −1.1 | 6/6 |
| | 0.2 | 15.5 | 194 | −0.5 | 6/6 |
| | 0.1 | 14.0 | 175 | −0.7 | 6/6 |
| Control | Saline | 8.0 | — | −0.4 | 10/10 |

Tumor inoculum: $10^6$ ascitic cells implanted i.p.
Host: $CDF_1$ ♀ mice.
Treatment: Daily, QD 1→9.
Tox: <4/6 survivors Day 5.
Evaluation: MST = median survival time.
Effect: T/C = (MST treated/MST control) × 100.
Criteria: % T/C ≧125 considered significant antitumor activity.

TABLE XV

Effect of Compound of Example 10 on P-388 Leukemia

| Material | Dose mg/kg/day | MST Days | Effect MST % T/C | Average Weight Change, g | Survivors Day 5 |
|---|---|---|---|---|---|
| NSC 38270 | 0.4 | 10.5 | 117 | −1.2 | 6/6 |
| | 0.2 | 10.5 | 117 | −0.8 | 6/6 |
| Anguidine | 1.6 | 17.5 | 195 | −0.7 | 6/6 |
| NSC 141537 | 0.8 | 15.0 | 167 | +0.7 | 6/6 |
| | 0.4 | 14.0 | 156 | +0.2 | 6/6 |
| | 0.2 | 12.0 | 133 | −0.3 | 6/6 |
| | 0.1 | 10.5 | 117 | +0.8 | 6/6 |
| | 0.05 | 10.5 | 117 | +0.4 | 6/6 |
| Compound of | 12.8 | 16.5 | 183 | −0.8 | 6/6 |
| Example 10 | 6.4 | 15.0 | 167 | +0.3 | 6/6 |
| | 3.2 | 16.0 | 178 | +0.8 | 6/6 |
| | 1.6 | 12.0 | 133 | −0.1 | 6/6 |
| | 0.8 | 12.0 | 133 | +0.2 | 6/6 |
| | 0.4 | 11.0 | 122 | +0.7 | 6/6 |

TABLE XV-continued

| Effect of Compound of Example 10 on P-388 Leukemia | | | | | |
|---|---|---|---|---|---|
| Material | Dose mg/kg/day | MST Days | Effect MST % T/C | Average Weight Change, g | Survivors Day 5 |
| Control | Saline | 9.0 | — | −1.8 | 10/10 |

Tumor inoculum: $10^6$ ascitic cells implanted ip
Host: $CDF_1$ ♂ mice.
Treatment: QD 1→9.
Tox: <4/6 survivors Day 5
Evaluation: MST = median survival time
Effect: % T/C = (MST treated/MST control) × 100.
Criteria: % T/C ≧125 considered significant antitumor activity

TABLE XVI

| Effect of Compound of Example 7 on P-388 Leukemia | | | | | |
|---|---|---|---|---|---|
| Material | Dose, IP mg/kg/inj | MST Days | Effect MST % T/C | Average Weight Change, g | Survivors Day 5 (3) |
| NSC 38270 | 0.4 | 9.0 | 100 | +0.3 | 6/6 |
| | 0.2 | 9.0 | 100 | +2.8 | 6/6 |
| Anguidine | 1.6 | 14.5 | 161 | +1.4 | 6/6 |
| NSC 141537 | 0.8 | 13.0 | 144 | +1.7 | 6/6 |
| | 0.4 | 12.0 | 133 | +1.8 | 6/6 |
| | 0.2 | 10.0 | 111 | +1.4 | 6/6 |
| | 0.1 | 9.0 | 100 | +2.3 | 6/6 |
| | 0.05 | 9.0 | 100 | +2.6 | 6/6 |
| Compound of | 12.8 | Tox | Tox | Tox | 0/6 |
| Example 7 | 6.4 | Tox | Tox | Tox | 0/6 |
| | 3.2 | Tox | Tox | Tox | 0/6 |
| | 1.6 | 18.0 | 200 | −1.3 | 4/6 |
| | 0.8 | 17.5 | 194 | −0.5 | 6/6 |
| | 0.4 | 15.0 | 167 | −0.1 | 6/6 |
| | 0.2 | 12.0 | 133 | +0.3 | 6/6 |
| | 0.1 | 12.0 | 133 | +0.3 | 6/6 |
| | 0.05 | 11.0 | 122 | +1.2 | 6/6 |
| | 0.025 | 10.0 | 111 | +1.1 | 5/6 |
| Control | Saline | 9.0 | — | +4.0 | 10/10 |

Tumor inoculum: $10^6$ ascites cells implanted i.p.
Host: $CDF_1$ ♀ mice.
Treatment: QD 1→9
Evaluation: MST = median survival time.
Effect: % T/C = (MST treated/MST control) × 100.
Criteria: % T/C ≧125 considered significant antitumor effect.

TABLE XVII

| Effect of Compound of Example 7 on L1210 Leukemia | | | | | |
|---|---|---|---|---|---|
| Material | Dose, IP mg/kg/day | MST Days | Effect MST % T/C | Average Weight Change, g | Survivors Day 5 (3) |
| Anguidine | 2.4 | 12.0 | 200 | +1.0 | 6/6 |
| NSC 141537 | 2.0 | 11.0 | 183 | +1.9 | 6/6 |
| | 1.6 | 10.0 | 167 | +1.4 | 6/6 |
| | 1.2 | 10.0 | 167 | +0.9 | 6/6 |
| | 0.8 | 10.0 | 167 | +0.9 | 6/6 |
| | 0.4 | 9.0 | 150 | +0.1 | 6/6 |
| | 0.2 | 8.0 | 133 | +1.3 | 6/6 |
| | 0.1 | 8.0 | 133 | +0.8 | 6/6 |
| Compound of | 2.4 | TOX | TOX | TOX | 1/6 |
| Example 7 | 2.0 | 7.0 | 117 | −1.2 | 3/6 |
| | 1.6 | 10.0 | 167 | −1.7 | 5/6 |
| | 1.2 | 9.5 | 158 | −1.1 | 6/6 |
| | 0.8 | 10.0 | 167 | −0.5 | 6/6 |
| | 0.4 | 10.0 | 167 | −0.8 | 6/6 |
| | 0.2 | 9.0 | 150 | −0.5 | 5/6 |
| | 0.1 | 8.0 | 133 | +0.5 | 6/6 |
| Control | Saline | 6.0 | — | +2.6 | 10/10 |

Tumor inoculum: $10^6$ ascites cells implanted, ip.
Host: $BDF_1$ ♀ mice.
Treatment: QD 1→9.
Evaluation: MST = median survival time.
Effect: % T/C = (MST treated/MST control). × 100
Criteria: % T/C ≧125 considered significant antitumor activity.

TABLE XVIII

| Effect of Compound of Example 7 on Lewis Lung Carcinoma | | | | | |
|---|---|---|---|---|---|
| Material | Dose, IP mg/kg/day | MST Days | Effect MST % T/C | Average Weight Change | Survivors Day 5 (60) |
| Anguidine | 1.6 | 21.0 | 124 | +2.2 | 10/10 |
| NSC 141537 | 0.8 | 21.0 | 124 | +1.8 | 10/10 |
| | 0.4 | 23.0 | 135 | +1.4 | 10/10 |
| Compound of | 2.0 | 21.5 | 126 | −0.5 | 6/10 |
| Example 7 | 1.5 | 21.5 | 126 | −0.3 | 10/10 |
| | 1.0 | 22.0 | 129 | +0.5 | 10/10 |
| | 0.5 | 22.0 | 129 | +1.2 | 10/10 |
| Control | Saline | 17.0 | — | −0.6 | 10/10 |

Tumor inoculum: $10^6$ tumor brei cells, ip.
Host; $BDF_1$ ♂ mice.
Treatment: QD 1→9.
Tox: <6/10 mice alive on Day 5.
Evaluation: MST = median survival time.
Effect: % T/C = (MST treated/MST control) × 100.
Criteria: % T/C ≧125 considered significant antitumor activity.

EXPLANATION

Each of the 14 derivatives of the present invention was evaluated in mice against P388 leukemia (ip) in parallel with anguidine itself, using a qd 1→9 dosing schedule (ip). The compounds were all found to be active and comparable to anguidine with respect to this tumor system.

The compound of Example 2 was evaluated twice against P388 leukemia (Tables VI and VII). As can be seen, the compound for some as yet unexplained reason appeared significantly more active in one test than the other.

Five compounds were evaluated in mice against L1210 leukemia (ip). All of them were active with maximum T/C values of between 150% and 175% using a qd 1→9 dosing schedule.

The compound of Example 7 was also evaluated in mice against Lewis lung carcinoma (ip). It produced a maximum T/C of 129% when given qd 1→9.

The following examples are not limiting but are intended to be illustrative of this invention. SKELLYSOLVE B is a commercially available petroleum solvent (Skelly Oil Co.) comprising isomeric hexanes and having a boiling point of 60°–68° C. The main component of SKELLYSOLVE B is n-hexane. Unless otherwise indicated, all melting points below are uncorrected, all temperatures are in degrees Celsius and all solvent percentages are by volume. The silica gel used in the examples (unless otherwise indicated) is SILICAR CC-7 (trademark of Mallinckrodt Chemical Works).

PREPARATION OF STARTING MATERIALS

PREPARATION 1

4β,15-Diacetoxy-3α-O-(2′-tetrahydropyranyl)-12,13-epoxytrichothec-9-ene

A mixture of 4β,15-diacetoxy-3α-hydroxy-12,13-epoxytrichothec-9-ene (12.81 g, 35 mmol), 2,3-dihydro-4H-pyran (17.5 ml, 189 mmol), and p-toluenesulfonic acid (70 mg, 0.35 mmol) in 150 ml of $CH_2Cl_2$ was stirred at room temperature for 2 h. After addition of 2.1 g of $K_2CO_3$, the reaction mixture was diluted with 400 ml of $CH_2Cl_2$ and washed with saturated $NaHCO_3$ solution and brine. Drying over $K_2CO_3$ and removal of the solvent gave a colorless oil which crystallized slowly from petroleum ether to give 11.30 g (72%) of solid. m.p.

93°–94° C.; IR(KBr): 2976, 1746, 1249, 1080, 1040, 988 $cm^{-1}$.

Anal. Calc'd for $C_{24}H_{34}O_8$: C, 63.98; H, 7.61. Found: C, 64.35; H, 7.58.

PREPARATION 2

3α,4β,15-Trihydroxy-12,13-epoxytrichothec-9-ene

4β,15-Diacetoxy-3α-hydroxy-12,13-epoxytrichothec-9-ene (15 g) was stirred for 20 minutes in 300 ml of methanol with 900 ml of 0.3N sodium hydroxide (Sigg et al. Helv. Chim. Acta, 48, 962–988 (1965). The solution was placed on a column containing 1 kg of DOWEX 50 (H+ cycle) prepared with 20% methanol in water. The column was eluted with 3 l of the same solvent, the eluate concentrated, and the residual aqueous solution freeze-dried. The powder was dissolved in methanol, mixed with 10 g of silica gel, and dried in vacuo. The dry silica gel mixture was placed on a column of fresh silica gel (2.5×100 cm) and eluted with methylene chloride with increasing amounts of methanol. Fractions appearing homogeneous on TLC plates were dried and crystallized from ethyl acetate. Yield: 7.3 g, m.p. 194°–195° C. IR(KBr): 3490, 3450, 3390, 2990–2900 (four peaks), 1675, 960 and 950 $cm^{-1}$. $[\alpha]_D^{22}=-15.4°$ (c=1, acetone).

Anal. Calc'd for $C_{15}H_{22}O_6$: C, 63.81; H, 7.86. Found: C, 63.71; H, 7.80.

Alternatively, the 3-O-tetrahydropyranyl derivative (Preparation 3 below) (1 g) was stirred for four hours in 115 ml of 95% ethanol and 23 ml of 1N HCl. The solution was azeotropically distilled with the addition of absolute ethanol, the concentrated ethanolic solution diluted with diethyl ether, and the resulting title product separated from ethyl acetate as a gum.

PREPARATION 3

4β,15-Dihydroxy-3α-O-(2'-tetrahydropyranyl)-12,13-epoxytrichothec-9-ene

To a solution of 4β,15-diacetoxy-3-O-(2'-tetrahydropyranyl)-12,13-epoxytrichothec-9-ene (1.067 g, 2.37 mmol) in 40 ml of tetrahydrofuran and methanol (5:3 v/v) was added 20 ml of 0.3N NaOH solution. After 2.5 h of stirring at room temperature, an additional 20 ml of 0.3N NaOH solution was introduced, and stirring was continued for 18.5 h. The resulting solution was diluted with $CH_2Cl_2$ (200 ml) and washed with water. The aqueous layer was reextracted with $CH_2Cl_2$ (2×50 ml). The combined $CH_2Cl_2$ layers were washed with brine and dried over $K_2CO_3$. Removal of the solvent gave 891 mg of foam, which was subsequently chromatographed on silica gel. Elution with 1% methanol-$CH_2Cl_2$ gave 46 mg (5%) of 15-acetoxy-4β-hydroxy-3α-O-(2'-tetrahydropyranyl)-12,13-epoxytrichothec-9-ene. A further elution with 5% methanol-$CH_2Cl_2$ gave 808 mg (93%) of the title compound as an amorphous solid. IR(KBr): 3457, 2943, 1445, 1135, 1125, 1078, 1035, 1020, 978, 957 $cm^{-1}$.

PREPARATION 4

15-Acetoxy-4β-hydroxy-3α-O-(2'-tetrahydropyranyl)-12,13-epoxytrichothec-9-ene To a solution of 4β,15-diacetoxy-3α-O-(2'-tetrahydropyranyl)-12,13-epoxytrichothec-9-ene (31.14 g, 69.2 mmol) in 800 ml of methanol and tetrahydrofuran (1:1 v/v) was added 400 ml of 1.31N $NH_4OH$ solution. After 3 days stirring at room temperature, 10 ml of concentrated $NH_4OH$ solution was added to the reaction mixture. Stirring was continued for an additional 4 days. The volume of the resulting solution was reduced to 500 ml. Extraction with $CH_2Cl_2$, washing with brine, and removal of the solvent gave 37 g of a slightly yellow oil. Chromatography on silica gel (elution with 1% methanol-$CH_2Cl_2$) gave 10.65 g (38%) of the title compound as an oil. The NMR and IR spectra of this material were consistent with the structure of the title compound. IR(KBr): 3430, 2970, 2950, 2875, 1744, 1720, 1270, 1248, 1126, 1080, 1040, 972 $cm^{-1}$.

EXAMPLE 1

A.

15-Chloroacetoxy-3α,4β-dihydroxy-12,13-epoxytrichothec-9-ene

Scirpentriol (3α,4β,15-trihydroxy-12,13-epoxytrichothec-9-ene) (7 g) was dissolved in 30 ml. of 2,6-lutidine and treated with 10.75 g of chloroacetic anhydride. After 18 hours the solution was poured on ice. The product of the usual isolation procedure was chromatographed on a column of silica gel (2×75 cm) by gradient elution with methylene chloride/methanol. The emerging (Rf 0.1, 0.35, 0.58, 0.80, 0.90) fractions were analyzed on TLC plates appropriately combined, dried and crystallized from ethyl acetate-ether-hexane. Fractions, Rf 0.35 gave 0.640 mg of title product. M.p. 173°. IR(KBr): 3520, 3380, 3800–2900 (4 peaks) 1725, 1295, 1060.

Anal. Calc'd for $C_{17}H_{23}O_6Cl$: C, 56.91; H, 6.46; Cl, 9.88. Found: C, 56.85; H, 6.39; Cl, 9.65.

B.

3α-Chloroacetoxy-4β,15-dihydroxy-12,13-epoxytrichothec-9-ene

Fractions Rf 0.58 from Example 1, Part A, gave 480 mg. of title product; m.p. 170°. IR(KBr): 3500, 3000–2900 (five peaks) 1758, 1745, 1210, 1170, 1055, 918 $cm^{-1}$.

Anal. Calc'd for $C_{17}H_{23}O_6Cl$: C, 56.91; H, 6.46; Cl, 9.88. Found: C, 57.03; H, 6.46; Cl, 9.85.

C.

3α,15-Bis(chloroacetoxy)-4β-hydroxy-12,13-epoxytrichothec-9-ene

Fractions Rf 0.8 from Example 1, Part A, gave 1.5 g title product; m.p. 161°. IR(KBr): 3480, 3060–2840 (seven peaks) 1765, 1735, 1295, 1200, 1165 $cm^{-1}$.

Anal. Calc'd for $C_{19}H_{24}O_7Cl_2$: C, 52.18; H, 5.99; Cl, 16.21. Found: C, 52.41; H, 5.55; Cl, 16.44.

D.

4β-Chloroacetoxy-3α,15-dihydroxy-12,13-epoxytrichothec-9-ene

Fractions with Rf 0.68 from Example 1, Part A, gave 205 mg of title product. The structure of the product was confirmed by PMR spectroscopy.

E.

3α,4β,15-Tri(chloroacetoxy)-12,13-epoxytrichothec-9-ene

Fractions with Rf 0.9 from Example 1, Part A, gave 95 mg. of title product. The structure of the product was confirmed by PMR spectroscopy.

EXAMPLE 2

4β,15-Bis(chloroacetoxy)-3α-hydroxy-12,13-epoxytrichothec-9-ene

A.

4β,15-Bis(chloroacetoxy)-3α-O-(2'-tetrahydropyranyl)-12,13-epoxytrichothec-9-ene A mixture of 4β,15-dihydroxy-3α-O-(2'-tetrahydropyranyl)-12,13-epoxytrichothec-9-ene (808 mg, 2.21 mmol), chloroacetic anhydride (1.132 g, 6.62 mmol) and pyridine (894 mg, 11.05 mmol) in 100 ml of $CH_2Cl_2$ was stirred at room temperature for 14 h. The reaction mixture was diluted with 200 ml of $CH_2Cl_2$ and washed with saturated $NaHCO_3$ solution, 1% HCl solution and brine. Drying over $K_2CO_3$ and removal of the solvent gave 1.058 g (92%) of foam which was homogeneous on TLC. A portion of this material was purified by silica gel chromatography (elution with 0.5% methanol-$CH_2Cl_2$) to furnish an analytical sample of title product. IR(KBr): 2955, 1762, 1740, 1290, 1186, 1172, 1129, 1080, 1039, 977 $cm^{-1}$.

B.

4β,15-Bis(chloroacetoxy)-3α-hydroxy-12,13-epoxytrichothec-9-ene

To a solution of 4β,15-bis(chloroacetoxy)-3α-O-(2'-tetrahydropyranyl)-12,13-epoxytrichothec-9-ene (858 mg, 1.65 mmol) in 100 ml of 95% ethanol was added 19 ml of 1N HCl solution. The resulting solution was stirred at room temperature for 24 hours. The reaction mixture was diluted with $CH_2Cl_2$ (300 ml) and washed with saturated $NaHCO_3$ solution and brine. Drying over $K_2CO_3$-$Na_2SO_4$ and removal of the solvent gave 600 mg of foam. Chromatography of this material on silica gel (elution with 1% methanol-$CH_2Cl_2$) gave 524 mg (73%) of 4β,15-bis(chloroacetoxy)-3α-hydroxy-12,13-epoxytrichothec-9-ene. An analytical sample was obtained by recrystallization from chloroform-diethyl ether, m.p. 139°-141° C. IR(KBr): 3450, 2970, 2913, 1758, 1742, 1327, 1293, 1192, 1173, 1083, 1008, 967 $cm^{-1}$.

Anal. Calc'd. for $C_{19}H_{24}O_7Cl_2$: C, 52.42; H, 5.56. Found: C, 52.31; H, 5.34.

Elution of the silica gel column with 2% methanol-$CH_2Cl_2$ gave 110 mg (15%) of 15-chloroacetoxy-3α,4β-dihydroxy-12,13-epoxytrichothec-9-ene.

EXAMPLE 3

15-Acetoxy-4β-chloroacetoxy-3α-hydroxy-12,13-epoxytrichothec-9-ene

A mixture of 15-acetoxy-4β-hydroxy-3α-O-(2'-tetrahydropyranyl)-12,13-epoxytrichothec-9-ene (785 mg, 1.92 mmol), chloroacetic anhydride (492 mg, 2.88 mmol) and pyridine (0.309 ml, 3.84 mmol) in 100 ml of $CH_2Cl_2$ was stirred at room temperature for 28.5 h. The reaction mixture was diluted with $CH_2Cl_2$ (200 ml) and washed with saturated $NaHCO_3$ solution and brine. Drying over $K_2CO_3$ and removal of the solvent gave 931 mg (100%) of a white foam. The NMR and IR spectra of this material were consistent with the structure of 15-acetoxy-4β-chloroacetoxy-3α-O-(2'-tetrahydropyranyl)-12,13-epoxytrichothec-9-ene.

To a solution of 15-acetoxy-4β-chloroacetoxy-3α-O-(2'-tetrahydropyranyl)-12,13-epoxytrichothec-9-ene (900 mg, 1.98 mmol) in 100 ml of 95% ethanol was added 19 ml of 1N HCl solution. After 10 h of stirring at room temperature, 200 ml of $CH_2Cl_2$ was added to the reaction mixture. The aqueous layer which separated was extracted with 25 ml of $CH_2Cl_2$. The combined $CH_2Cl_2$ layers were washed with saturated $NaHCO_3$ solution and brine. Drying over $K_2CO_3$-$Na_2SO_4$ and removal of the solvent gave 662 mg of foam. Chromatography on silica gel (elution with 0.5% methanol-$CH_2Cl_2$) gave 350 mg (44%) of the title compound. Recrystallization from diethyl ether furnished the analytical sample; m.p. 166°-167.5° C. IR(KBr): 3500, 3040, 3020, 2989, 2918, 1754, 1736, 1378, 1330, 1260, 1208, 1167, 1074, 1052, 960 $cm^{-1}$.

Anal. Calc'd for $C_{19}H_{25}O_7Cl$: C, 56.83; H, 6.29. Found: C, 57.12; H, 6.29.

EXAMPLE 4

15-(trans-2'-Butenoyloxy)-3α,4β-dihydroxy-12,13-epoxytrichothec-9-ene

A solution containing 366 mg (1 mmol) of 3α-O-(2'-tetrahydropyranyl)-4β,15-dihydroxy-12,13-epoxytrichothec-9-ene and 395 mg (5 mmol) of dry pyridine in 50 ml of $CH_2Cl_2$ (previously dried over 4 Å molecular sieves) was cooled at 5° C. To the stirred solution was added dropwise 261 mg (2.5 mmol) of trans-2-butenoic acid chloride and, after completion of the addition, the mixture was stirred for 1 hr at 5° C. and for 16 h at ambient temperature. The solution was diluted with 50 ml of $CH_2Cl_2$ and was successively washed with saturated aqueous $NaHCO_3$, brine, 1% aqueous HCl and brine. The organic phase was dried over $Na_2SO_4$ and the solvent was evaporated under reduced pressure to provide 360 mg of a gum. This was dissolved in 50 ml of 95% ethanol and to it was added 5 ml of 2N HCl. After the solution had been stored at room temperature for 22 h, it was diluted with 100 ml of $CH_2Cl_2$ and was washed successively with $H_2O$, saturated aqueous $NaHCO_3$ and brine. The organic phase was dried over $Na_2SO_4$ and the solvent was evaporated under reduced pressure to provide 260 mg of gum. This was chromatographed on 20 g of silica gel using 1% methanol in $CH_2Cl_2$ as the solvent. The first product eluted was 4β,15-bis-(trans-2'-butenoyloxy)-3α-hydroxy-12,13-epoxytrichothec-9-ene (26 mg) followed by 22 mg of 4β(trans-2'-butenoyloxy)-3α,15-dihydroxy-12,13-epoxytrichothec-9-ene and then 147 mg of the title compound which was crystallied from $CHCl_3$-SKELLYSOLVE B as a white solid of mp 83°-86°. IR(KBr): 3440, 2970, 1725, 1190, 1110, 1085, 965 $cm^{-1}$.

Anal. Calc'd for $C_{19}H_{26}O_6.0.5H_2O$: C, 63.49; H, 7.57. Found: C, 63.54; H, 7.43.

EXAMPLE 5

4β,15-Bis-(trans-2'-butenoyloxy)-3α-hydroxy-12,13-epoxytrichothec-9-ene

Repetition of the above experiment using 6 equivalents of trans-2-butenoic acid chloride gave the title compound as a hygroscopic white foam. IR(KBr): 3420, 2970, 1720, 1310, 1260, 1185, 965 $cm^{-1}$. In addition, there was obtained 4β(trans-2'-butenoyloxy)-3α,15-dihydroxy-12,13-epoxytrichothec-9-ene as a cream solid of m.p. 60°-62° C. IR(KBr): 3460, 2960, 1710, 1315, 1190, 1105, 1080, 955 $cm^{-1}$.

Anal. Calc'd for $C_{19}H_{26}O_6.0.25H_2O$: C, 64.30; H, 7.53. Found: C, 64.19; H, 8.06.

EXAMPLE 6

15-(2'-methylpropenoyloxy)-3α,4β-dihydroxy-12,13-epoxytrichothec-9-ene

To a solution of 366 mg (1 mmol) of 3α-O-(2'-tetrahydropyranyl)-4β,15-dihydroxy-12,13-epoxytrichothec-9-ene and 395 mg (5 mmol) of dry pyridine in 50 ml of methylene chloride (dried over 4 Å molecular sieves) was added with stirring 261 mg (2.5 mmol) of freshly distilled 2-methylpropenoic acid chloride. The solution was stored at 22° C. for 17 h and was then treated with an additional 261 mg (2.5 mmol) of the acid chloride. After a further 22 h at 22° C., the solution was worked up as described in Example 4 and the residue was chromatographed on 20 g of silica gel. 2-Methylpropenoic acid anhydride was eluted using 1% methanol in $CH_2Cl_2$. The solvent was changed to methanol to elute 230 mg of white foam which was hydrolyzed as described above (Example 4) to give 189 mg of a foam. This was chromatographed on 20 g silica gel using 1% methanol in $CH_2Cl_2$ as the solvent. Minor products were eluted and the solvent was changed to 20% methanol in $CH_2Cl_2$ to afford 116 mg (33%) of the title compound as a foam which crystallized from $CH_2Cl_2$-SKELLYSOLVE B as a pale pink solid of m.p. 79°-81° C. IR(KBr): 3440, 2960, 1715, 1165, 1080, 955 $cm^{-1}$.

Anal. Calc'd for $C_{19}H_{26}O_6.0.5H_2O$: C, 63.49; H, 7.57. Found: C, 63.36; H, 7.40.

EXAMPLE 7

4β-(Chloroacetoxy)-15-(2'-methylpropenoyloxy)-3α-hydroxy-12,13-epoxytrichothec-9-ene

A.

3α-O-(2'-Tetrahydropyranyl)-15-(2'-methylpropenoyloxy)-4β-hydroxy-12,13-epoxytrichothec-9-ene A solution containing 3.66 g (0.01 mol) of 3α-O-(2'-tetrahydropyranyl)-4β,15-dihydroxy-12,13-epoxytrichothec-9-ene, 3.95 g (0.05 mol) of pyridine and 2.61 g (0.025 mol) of freshly distilled 2-methylpropenoic acid chloride in 250 ml of dry methylene chloride was stirred for 16 h at 22° C. An additional 2.61 g (0.025 mol) of the acid chloride was added and stirring was continued for 6 h. The solution was diluted with $CH_2Cl_2$ and was washed in succession with saturated aqueous $NaHCO_3$, brine, 1% aqueous HCl and brine. The organic phase was dried over $Na_2SO_4$ and the solvent evaporated under reduced pressure to give 5.36 g of an oil. This was chromatographed on 100 g of silica gel using 1% methanol in $CH_2Cl_2$ as the solvent. 2-Methylpropenoic acid anhydride was first eluted, followed by 615 mg of a foam which was hydrolysed as before (Example 4) in 67.5 ml of 95% ethanol and 13.5 ml of 1N HCl. The usual work-up gave 590 mg of gum from which, by chromatography, 198 mg of 4β,15-bis-(2'-methylpropenoyloxy)-3α-hydroxy-12,13-epoxytrichothec-9-ene was isolated as a hygroscopic foam IR(KBr): 3500, 2960, 1720, 1165, 1080, 960 $cm^{-1}$; which was identified by its NMR spectrum. The next fraction from this chromatography afforded 4β-(2'-methylpropenoyloxy)-3α,15-dihydroxy-12,13-epoxytrichothec-9-ene as colorless crystals of m.p. 175°-176° C. IR(KBr): 3510, 3460, 2500, 1690, 1330, 1300, 1170, 1080, 1060, 910, 900 $cm^{-1}$.

Anal. Calc'd for $C_{19}H_{26}O_6.0.25H_2O$: C, 64.30; H, 7.53. Found: C, 64.24; H, 7.14.

From the chromatographic separation of the tetrahydropyranyl ethers (above) there was next obtained 810 mg of a foam which was re-chromatographed on fresh silica gel (20 g) using the same solvent system to provide 3α-O-(2'-tetrahydropyranyl)-15-(2'-methylpropenoyloxy)-4β-hydroxy-12,13-epoxytrichothec-9-ene as a foam.

B.

4β-(Chloroacetoxy)-15-(2'-methylpropenoyloxy)-3α-hydroxy-12,13-epoxytrichothec-9-ene To a stirred solution of 164 mg (0.38 mmol) of 3α-O-(2'-tetrahydropyranyl)-15-(2'-methylpropenoyloxy)-4β-hydroxy-12,13-epoxytrichothec-9-ene in 25 ml of dry $CH_2Cl_2$ were added in succession 36 mg (0.46 mmol) of pyridine and 78 mg (0.46 mmol) of chloroacetic anhydride. The solution was stored for 17 h at 22° C. The solution was worked up as before and hydrolysed as usual with 27 ml of 95% ethanol and 5.4 ml of 1N HCl. After work-up as before there was obtained a gum which was triturated with SKELLYSOLVE B to provide a hydroscopic solid of m.p. 58°-60° C. IR(KBr): 2960, 1755, 1715, 1320, 1295, 1165, 1085, 955 $cm^{-1}$.

Anal. Calc'd for $C_{21}H_{27}ClO_7$: C, 59.08; H, 6.38. Found: C, 60.48; H, 6.66.

EXAMPLE 8

15-(2'-Chloropropionyloxy)-3α,4β-dihydroxy-12,13-epoxytrichothec-9-ene

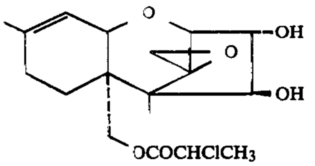

To a mixture of scirpentriol (1.12 g) in 2,6-lutidine (10 ml), there was added with cooling 1 ml of 2-chloropropionyl chloride. After 24 hours at room temperature the solution was poured on ice, and the mixture was extracted with 3×15 ml of ethyl acetate. The organic layer was washed with water and dilute sodium bicarbonate. After evaporation of the dried solvent, there remained 1.1 g of an oil. This was dissolved in 8 ml of benzene and placed on a silica gel column (Grace, 1.5×49 cm). The column was eluted with benzene containing increasing proportions of methanol. The title compound emerged with 2.5% methanol and appeared homogeneous on TLC plates ($SiO_2$) developed with ethyl acetate-toluene (3:1 v/v). Yield: 28.8 mg.

The NMR spectrum ($CDCl_3$, 100 MHz) of the product showed the following peaks:

| ppm | |
|---|---|
| 0.7 (s, 3H) | C-14 |
| 1.7-2.0 (m, 10H) | C-16, C-7, C-8, $CH_3CHCl$ |
| 2.8-3.1 (dd, 2H) | C-13 |
| 3.7 (d, 1H) | C-2 |
| 3.9-4.1 (dd, 2H) | C-15 |
| 4.3-4.5 (m, 3H) | C-3, C-4, C-11 |
| 4.4-4.6 ((g, 1H) | $CHClCH_3$ |
| 5.5 (d, 1H) | C-10 |

NMR showed that C-15 was acylated (C-15 protons appeared at 3.9-4.1 ppm); protons at C-3 and C-4 appeared approximately at 4.5 ppm indicating that they were not acylated.

EXAMPLE 9

15-Benzoyloxy-3α,4β-dihydroxy-12,13-epoxytrichothec-9-ene

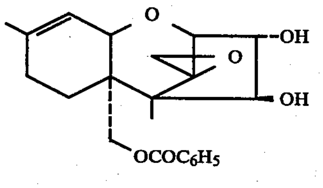

3α,4β,15-Tribenzoyl-12,13-epoxytrichothec-9-ene (1.4 g) was hydrolyzed for 4.5 hours in a solution of 230 ml of methanol, 19 ml of concentrated ammonium hydroxide and 31 ml of water. The mixture was concentrated and extracted with benzene (3×50 ml). The volume was reduced to 25–30 ml which was placed on a silica gel column (Grace, 2×49 cm) and eluted with benzene containing increments of methanol. The fractions were monitored on TLC plates ($SiO_2$) with benzene-methanol (188:12 v/v) as developer. Spots were visualized with an alkaline permanganate spray. The fraction emerging at 2% methanol yielded 56 mg of the pure 4β,15-dibenzoate; at 3% methanol 221 mg of the title compound was obtained.

NMR ($CDCl_3$, 100 MHz) showed the following peaks:

| ppm | |
|---|---|
| 0.8 (s, 3H) | C-14 |
| 1.7 (s, 3H) | C-16 |
| 2.0 (m, 4H) | C-7, C-8 |
| 2.7–3.0 (dd, 2H) | C-13 |
| 3.9–4.3 (m, 3H) | C-3, C-4, C-11 |
| 4.0–4.4 (m, 2H) | C-15 |
| 5.5 (d, 1H) | C-10 |
| 7.1–8 (m, 5H) | benzoyl |

C-3 and C-4 protons appeared at 3.9–4.3 ppm indicating that they were not acylated.

The starting material, 3α,4β,15-tribenzoyloxy-12,13-epoxytrichothec-9-ene, in this experiment was prepared by acylating scirpentriol with benzoyl chloride according to the following procedure:

To scirpentriol (840 mg) dissolved in 6 ml of pyridine, there was added 1.3 g of benzoyl chloride. After 24 hours at room temperature the solution was added to ice. The usual work-up gave a solid which was crystallized from ether-hexane to give 350 mg of 3α,4β,15-tribenzoyloxy-12,13-epoxytrichothec-9,10-ene.

The NMR spectrum ($CDCl_3$, 100 MHz) of the product showed the following peaks:

| ppm | |
|---|---|
| 1.05 (s, 3H) | C-14 |
| 1.75 (s, 3H) | C-16 |
| 2.10 (m, 4H) | C-7, C-8 |
| 2.95–3.25 (dd, 2H) | C-13 |
| 4.2 (d, 1H) | C-11 |
| 4.5–4.8 (m, 2H) | C-15 |
| 5.5–5.6 (d, 1H) | C-10 |
| 5.7 (m, 1H) | C-3 |
| 6.2 (d, 1H) | C-4 |
| 7.3–8.2 (m, 15H) | (benzoyl) |

The compound contains 3 benzoyl groups; protons at C-3, C-4 and C-15 are on carbons bearing acylated hydroxyl groups.

EXAMPLE 10

9,10β-Epoxy-15-(trans-2′-butenoyloxy)-3α,4β-dihydroxy-12,13-epoxytrichothec-9-ene

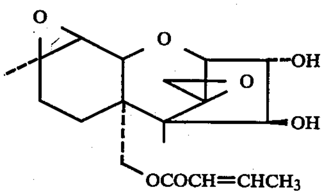

A solution containing approximately equimolar amounts of the bis-ester of Example 5 and m-chloroperbenzoic acid in $CH_2Cl_2$ was stirred at room temperature for 72 hours. The resulting solution was washed in succession with 10% aqueous $Na_2SO_3$, saturated aqueous $NaHCO_3$ and brine. The organic phase was dried over $Na_2SO_4$ and the solvent was evaporated under reduced pressure to give the title product, m.p. 83°–85° C.

Anal. Calc'd. for $C_{19}H_{26}O_7 0.5H_2O$: C, 60.78; H, 7.25. Found: C, 60.52; H, 7.25.

We claim:

1. The compound having the formula

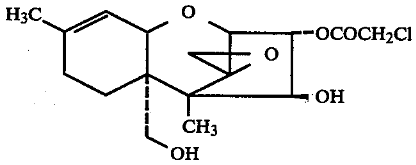

* * * * *